(12) United States Patent
Tsaur

(10) Patent No.: US 6,789,971 B2
(45) Date of Patent: Sep. 14, 2004

(54) MULTI-CHANNEL CONTAINER

(76) Inventor: Garry Tsaur, 19222 Tranbarger St., Rowland Heights, CA (US) 91748

( * ) Notice: Subject to any disclaimer, the term of this patent is extended or adjusted under 35 U.S.C. 154(b) by 0 days.

(21) Appl. No.: 09/973,637

(22) Filed: Oct. 9, 2001

(65) Prior Publication Data
US 2003/0068189 A1 Apr. 10, 2003

(51) Int. Cl.$^7$ .......................... B43K 5/14; A46B 11/00; A61M 35/00
(52) U.S. Cl. ................... 401/133; 401/132; 401/44; 401/47; 604/3
(58) Field of Search ..................... 401/133, 132, 401/47, 44, 46; 604/1, 2, 3; 222/541.1, 541.3, 541.4, 541.6; 206/824

(56) References Cited

U.S. PATENT DOCUMENTS

| | | | | | |
|---|---|---|---|---|---|
| 1,332,985 | A | * | 3/1920 | Jarrett | 206/222 |
| 2,499,313 | A | * | 2/1950 | Hoag | 222/129 |
| 2,861,719 | A | * | 11/1958 | Trotter | 222/144 |
| 3,263,863 | A | * | 8/1966 | Hoag | 222/107 |
| 3,757,782 | A | * | 9/1973 | Aiken | 401/132 |
| 3,981,304 | A | * | 9/1976 | Szpur | 604/3 |
| 4,218,155 | A | * | 8/1980 | Weidner | 401/132 |
| 4,740,194 | A | * | 4/1988 | Barabino et al. | 401/132 |
| 5,120,301 | A | * | 6/1992 | Wu | 401/132 |
| 5,490,736 | A | * | 2/1996 | Haber et al. | 401/132 |

* cited by examiner

Primary Examiner—David J. Walczak
(74) Attorney, Agent, or Firm—Joe Nieh

(57) ABSTRACT

The multi-channel container comprises of a multi-channel single-tube sealed container and applicator that defines multiple channels within its body that may contain different substances in each channel and that is sealed on both ends. A score is formed at a predetermined distance from each sealed end of the multi-channel single-tube sealed container and applicator such that when the multi-channel single-tube sealed container and applicator is bent it will break open at the score discharging the substances in the channels.

The multi-channel container is a multi-channel single-tube sealed container and applicator that is easy to package, convenient, easy to use, easy to transport, sanitary, economical, and self-contained. The multi-channel container is not only a container but can also be used as the applicator. Furthermore, the multi-channel container eliminates the tedious task of measuring the proper proportion of the substances required for application.

8 Claims, 6 Drawing Sheets

MULTI-CHANNEL CONTAINER

BACKGROUND

1. Field of Invention

The present invention relates to a multi-channel single-tube sealed container and applicator.

2. Description of Related Art

Many medications, chemicals, and adhesives require the mixture of two or more substances just before application to form the final product that will be applied or used. Common examples of these types of products are hair dyes and quick dry adhesives. The substances must be kept separate until just before the product is to be applied or used. Generally the substances must be carefully mixed in a fixed proportion. Often times, once the substances are exposed to the atmosphere, it must be used completely, and any remaining substances that are not used must be discarded and cannot be stored. For these reasons, most of the packaging for these types of products are sealed in separate small airtight containers.

SUMMARY OF THE INVENTION

The present invention is a multi-channel single-tube sealed container and applicator that is easy to package, convenient, easy to use, easy to transport, sanitary, economical, and self-contained. The present invention is not only a container but can also be used as the applicator. Furthermore, the present invention eliminates the tedious task of measuring the proper proportion of the substances required for application.

The present invention comprises of a multi-channel single-tube sealed container and applicator that defines multiple channels within its body that may contain different substances in each channel and that is sealed on both ends. A score is formed at a predetermined distance from each sealed end of the multi-channel single-tube sealed container and applicator such that when the multi-channel single-tube sealed container and applicator is bent it will break open at the score discharging the substances in the channels.

DETAILED DESCRIPTION OF THE PREFERRED EMBODIMENT

Figure 1:
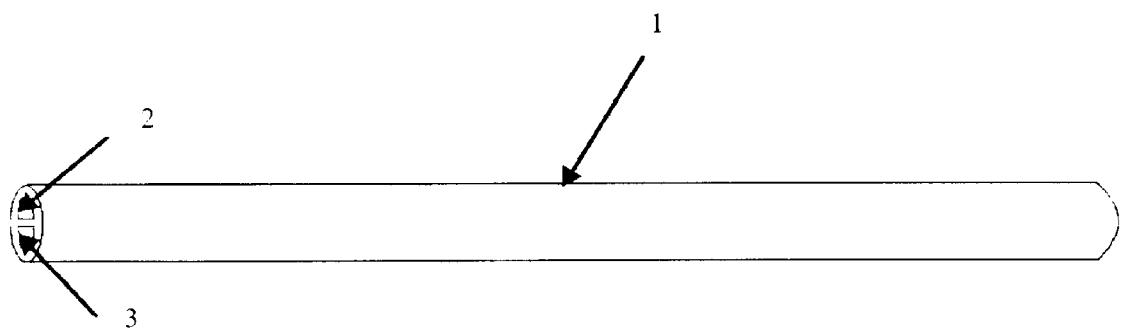
FIG. 1 shows the housing 1 of the multi-channel single-tube sealed container and applicator before the ends 5, 6 are sealed.

FIG. 1 shows the preferred embodiment of the housing 1 of the multi-channel single-tube sealed container and applicator before either of its two ends 5, 6 are sealed. The preferred embodiment of the multi-channel single-tube sealed container and applicator has a housing 1 that is in the shape of an elongated cylinder with two semi-spherical channels 2, 3 through the length of the housing 1 defined by the housing 1 and a dividing wall 4 within the housing 1.

Figure 2:
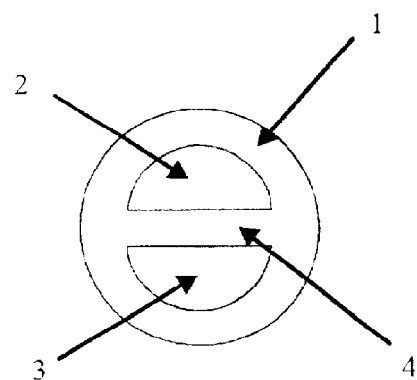
FIG. 2 shows the end view of the housing 1 of the multi-channel single-tube sealed container and applicator.

FIG. 2 shows the end view of the preferred embodiment of the multi-channel single-tube sealed container and applicator. The preferred embodiment of the multi-channel single-tube sealed container and applicator has a housing 1 that is in the shape of an elongated cylinder with two semi-spherical channels 2, 3 through the length of the housing 1 defined by the housing 1 and a dividing wall 4 within the housing 1.

Figure 3:
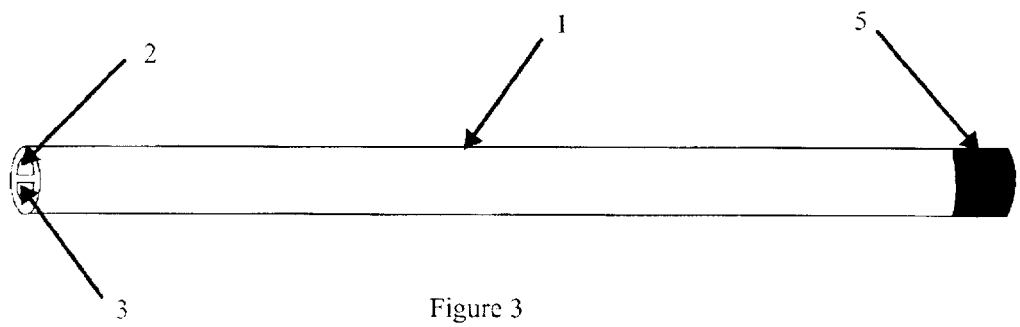
FIG. 3 shows the multi-channel single-tube sealed container and applicator with one of its ends 5 sealed.

FIG. 3 shows the preferred embodiment of the multi-channel single-tube sealed container and applicator with one of its two ends 5 sealed.

Figure 4:
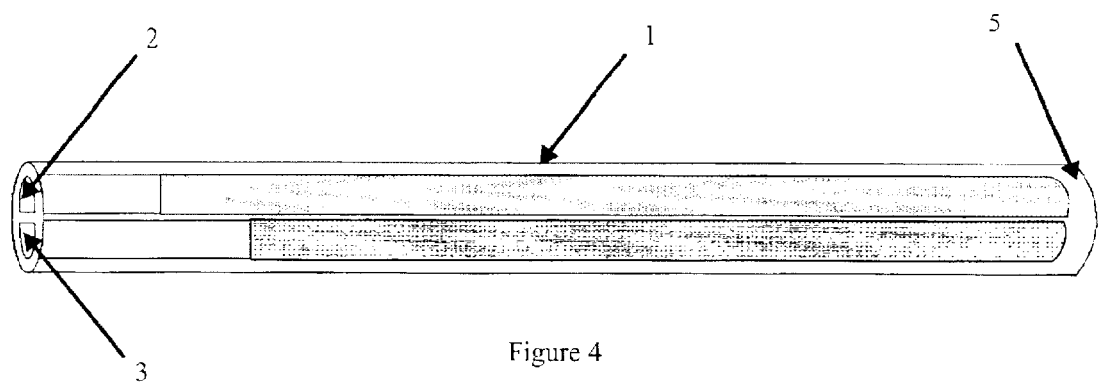
FIG. 4 shows the multi-channel single-tube sealed container and applicator with one of its ends 5 sealed and its channels 2, 3 filled with different substances.

FIG. 4 shows the preferred embodiment of the multi-channel single-tube sealed container and applicator with its channels 2, 3 filled with different substances. The proportion of the substances can be controlled by filling the channels 2, 3 to different heights.

Figure 5:
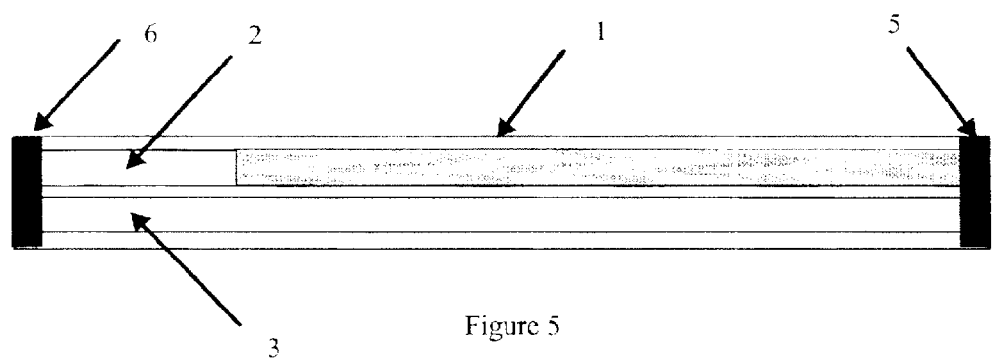
FIG. 5 shows the multi-channel single-tube sealed container and applicator with both ends 5, 6 sealed after its channels 2, 3 are filled with different substances.

FIG. 5 shows the preferred embodiment of the multi-channel single-tube sealed container and applicator with both of its ends 5, 6 sealed after its channels 2, 3 are filled with different substances.

Figure 6:
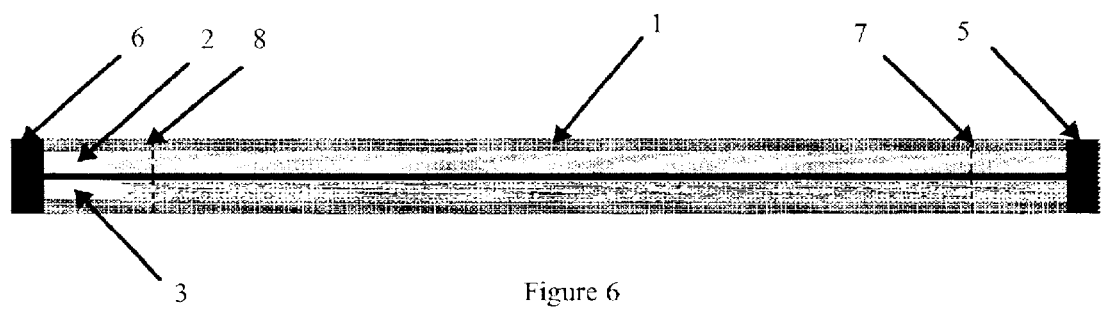
FIG. 6 shows the multi-channel single-tube sealed container and applicator with scores 7, 8 formed at a predetermined distance from each sealed end 5, 6.

FIG. 6 shows the preferred embodiment of the multi-channel single-tube sealed container and applicator with a score 7, 8 formed at a predetermined distance from each sealed end 5, 6.

Figure 7:
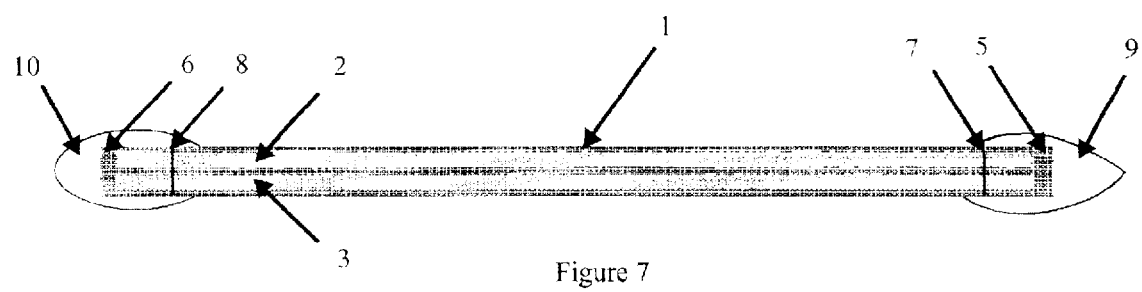
FIG. 7 shows the multi-channel single-tube sealed container and applicator with a cotton swab 9, 10 attached to each of its sealed end 5, 6 enclosing the score 7, 8.

FIG. 7 shows the preferred embodiment of the multi-channel single-tube sealed container and applicator with a cotton swab 9, 10 attached to each of its sealed end 5, 6 enclosing the score 7, 8 at each of the sealed end 5, 6. The cotton swabs 9, 10 may be in a rounded 10 or a pointed 9 shape at both ends 5, 6 or the cotton swab 9, 10 may be in a rounded shape 10 at one end 6 and in a pointed shape 9 at the other end 5.

Figure 8:
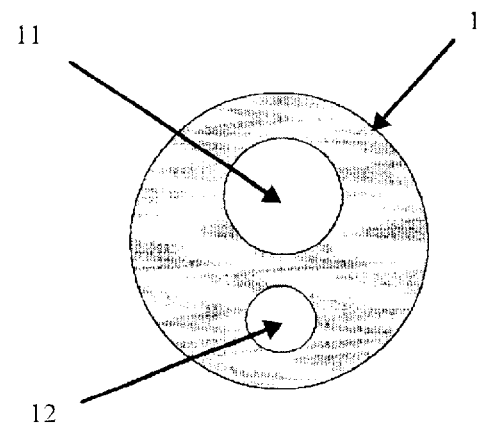
FIG. 8 shows the end view of another embodiment of the multi-channel single-tube sealed container and applicator.

FIG. 8 shows the end view of another embodiment of the multi-channel single-tube sealed container and applicator. The channels 2, 3 though the housing may have a circular profile or any other predetermined profile. The proportion of the substances may be controlled by varying the cross-sectional area of the channels 2, 3.

Figure 9:
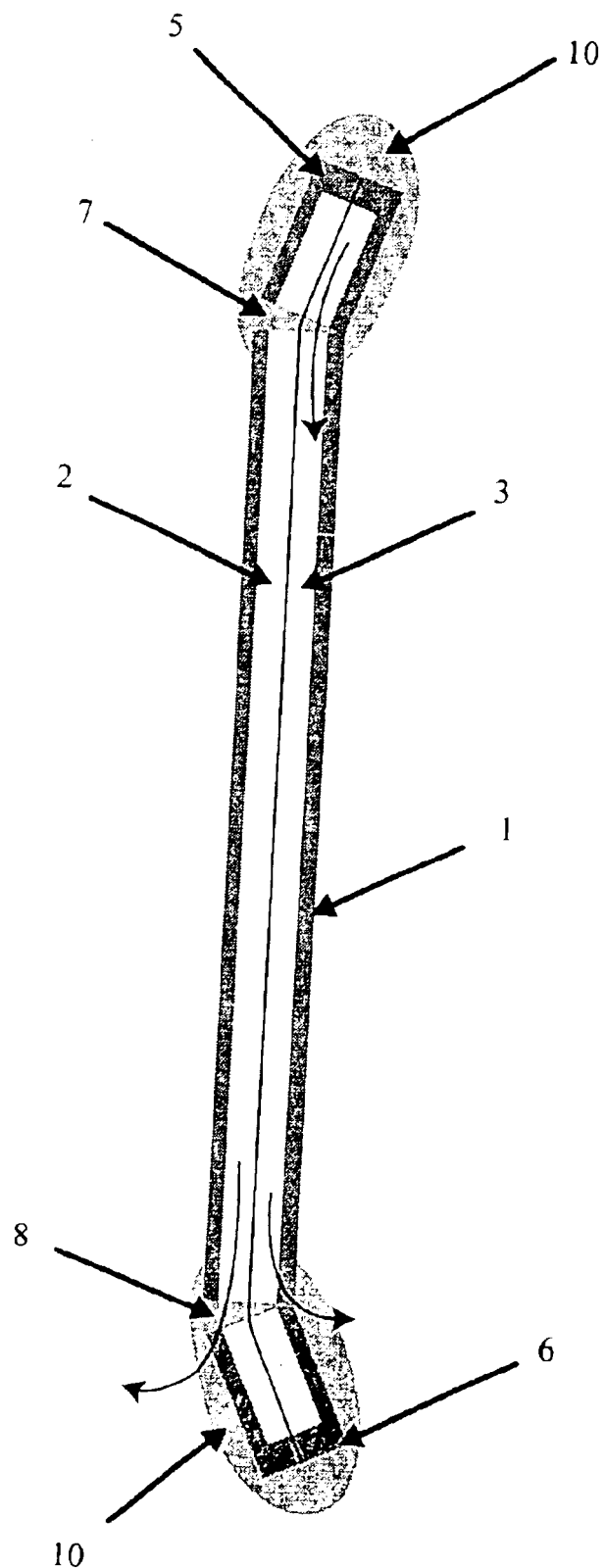
FIG. 9 shows the multi-channel single-tube sealed container and applicator with both of its sealed ends 5, 6 broken allowing the substance to be discharged from their respective channels 2, 3 into the cotton swab 10 at the end of the multi-channel single-tube sealed container and applicator.

FIG. 9 shows the preferred embodiment of the multi-channel single-tube sealed container and applicator with both of its sealed ends 5, 6 broken at the scores 7, 8 thereby allowing the substance within the channels 2, 3 to be discharged from their respective channels 2, 3 into the cotton swab 10 at the end of the housing 1.

Figure 10:
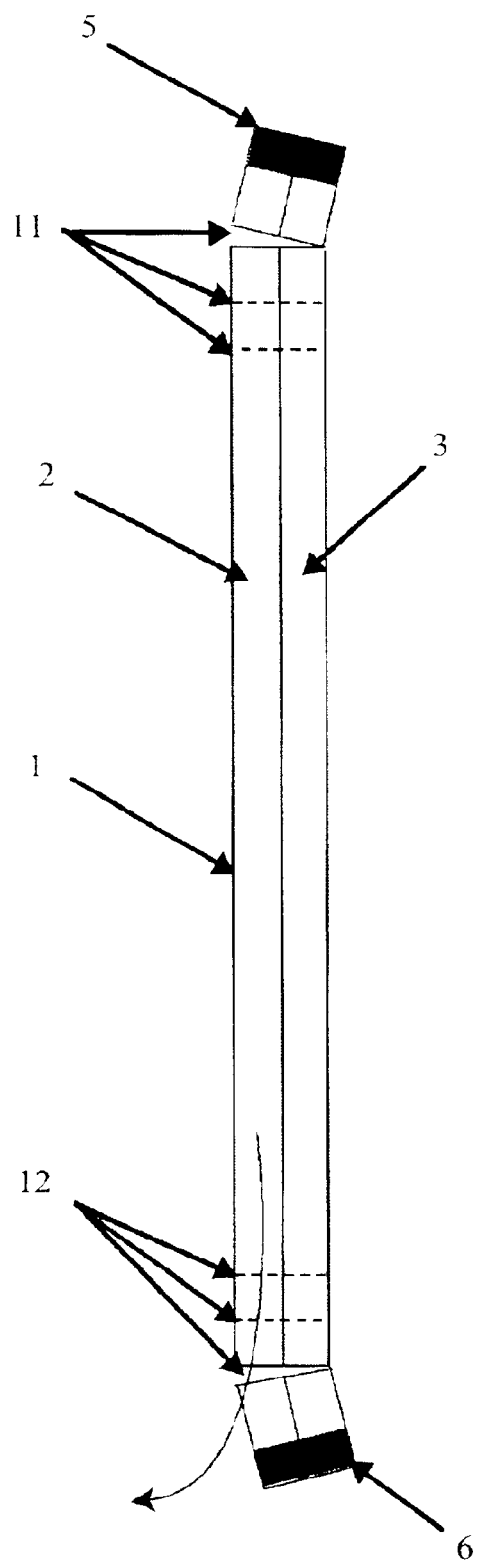
FIG. 10 shows another embodiment of the multi-channel single-tube sealed container and applicator with multiple scores 11, 12 formed perpendicular to the housing at predetermined distances from each sealed end 5, 6.

FIG. 10 shows another embodiment of the multi-channel single-tube sealed container and applicator with multiple scores 11, 12 formed perpendicular to the housing 1 at predetermined distances from each sealed end 5, 6. The amount of substance released may be controlled by breaking the sealed ends 5, 6 at the appropriate scores 11, 12 on the end of the housing 1 that the substances are accumulated. If the inside diameter of the housing 1 is sufficiently small, when the end of the housing 1 where the substances are accumulated are broken, the substances accumulated in the broken end are trapped and cannot be discharged due to surface tension of the substance and the atmospheric pressure, while the substance in the housing 1 will be discharged when the other end of the housing 1 is broken.

Figure 11:
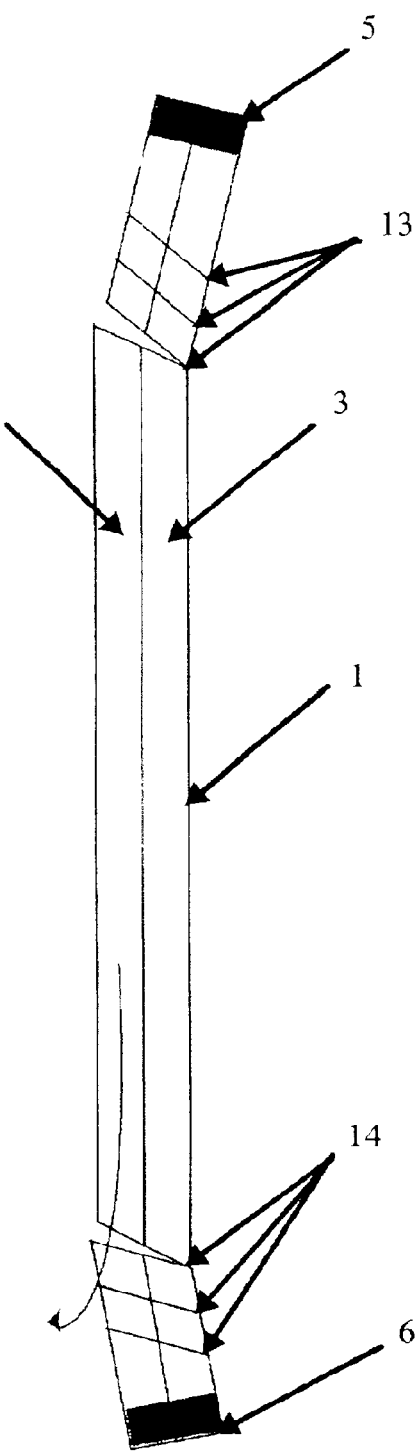
FIG. 11 shows another embodiment of the multi-channel single-tube sealed container and applicator with multiple scores 13, 14 formed at a predetermined angle to the housing at predetermined distances from each sealed end 5, 6.

FIG. 11 shows another embodiment of the multi-channel single-tube sealed container and applicator with multiple scores 13, 14 formed at predetermined angle to the housing 1 at predetermined distances from each sealed end 5, 6. The amount of substance released may be controlled by breaking the sealed ends 5, 6 at the appropriate score 13, 14 on the end of the housing 1 that the substances are accumulated. When the end of the housing 1 that the substances are accumulated are broken, the substances accumulated in the broken end are trapped and cannot be discharged, while the substances in the housing 1 will be discharged when the other end of the housing 1 is broken.

What is claimed is:

1. A multi-channel single-tube sealed container and applicator comprising:

a housing with a first end and a second end wherein said housing encloses multiple channels each extending from said first end to said second end and each capable of containing a substance and is sealed on both ends and with a score formed at a predetermined distance from each end of the housing wherein the substances in each channel may be discharged through one end when the housing is broken open at the scores.

2. A multi-channel single-tube sealed container and applicator as in claim 1, wherein each of the two ends of the housing is surrounded by a cotton swab.

3. A multi-channel single-tube sealed container and applicator as in claim 2, wherein said cotton swab is rounded in shape.

4. A multi-channel single-tube sealed container and applicator as in claim 2, wherein said cotton swab is pointed in shape.

5. A multi-channel single-tube sealed container and applicator comprising:

a housing with a first end and a second end wherein said housing encloses multiple channels each extending from said first end to said second end and each capable of containing a substance and is sealed on both ends and with multiple scores formed at multiple predetermined distances from each end of the housing wherein the substances in each channel may be discharged through one end when the housing is broken oven at the scores.

6. A multi-channel single-tube sealed container and applicator as in claim 5, wherein each of the two ends of the housing is surrounded by a cotton swab.

7. A multi-channel single-tube sealed container and applicator as in claim 6, wherein said cotton swab is rounded in shape.

8. A multi-channel single-tube sealed container and applicator as in claim 6, wherein said cotton swab is pointed in shape.

* * * * *